United States Patent [19]

Berg et al.

[11] Patent Number: 4,693,787
[45] Date of Patent: Sep. 15, 1987

[54] SEPARATION OF T-AMYL ALCOHOL FROM ISOBUTANOL BY EXTRACTIVE DISTILLATION

[76] Inventors: Lloyd Berg, 1314 S. 3rd Ave.; Michael J. Shanahan, 8929 Gold Dust Trail, both of Bozeman, Mont. 59715

[21] Appl. No.: 20,350

[22] Filed: Mar. 2, 1987

[51] Int. Cl.$^4$ .................... B01D 3/40; C07C 29/84
[52] U.S. Cl. ...................................... 203/51; 203/56; 203/57; 203/60; 203/61; 203/64; 568/913
[58] Field of Search ............... 203/57, 51, 61, 64, 203/56, 60; 568/913, 918

[56] References Cited

U.S. PATENT DOCUMENTS

| | | | |
|---|---|---|---|
| 1,862,706 | 6/1932 | Ricard et al. | 203/16 |
| 2,483,246 | 9/1949 | Stribley | 203/60 |
| 2,551,584 | 5/1951 | Carlson et al. | 203/51 |
| 2,559,519 | 7/1951 | Smith et al. | 203/64 |
| 2,570,205 | 10/1951 | Carlson et al. | 203/58 |
| 2,595,805 | 5/1952 | Morrell et al. | 203/84 |
| 4,366,032 | 12/1982 | Mikitenko et al. | 203/58 |

Primary Examiner—Wilbur Bascomb

[57] ABSTRACT t-Amyl alcohol and isobutanol cannot be separated from each other by distillation because of the proximity of their boiling points. t-Amyl alcohol can be readily separated form isobutanol by using extractive distillation in which the extractive agent is a higher boiling organic compound or a mixture of two or more of these. Typical examples of effective agents are: dimethylsulfoxide; dimethylsulfoxide and N,N-dimethylacetamide; dimethylsulfoxide, dimethylformamide and phthalic anhydride.

2 Claims, No Drawings

SEPARATION OF T-AMYL ALCOHOL FROM ISOBUTANOL BY EXTRACTIVE DISTILLATION

FIELD OF THE INVENTION

This invention relates to a method for separating t-amyl alcohol from isobutanol using certain higher boiling liquids as the extractive agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification columns alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

Isobutanol and t-amyl alcohol are two of the most widely used alcohols in commerce today. When they are used as solvents, they frequently end up as a mixture of solvents. Whenever practical, it is mandatory to recover the solvent and re-use it. t-Amyl alcohol boils at 102.4° C., isobutanol at 108.1° C. and these two have a relative volatility of 1.165, making it difficult to separate these two by rectification. Extractive distillation would be an attractive method of effecting the separation of t-amyl alcohol from isobutanol if agents can be found that (1) will alter the relative volatility between t-amyl alcohol and isobutanol, (2) form no azeotropes with t-amyl alcohol or isobutanol and (3) are easy to recover from isobutanol, that is boil sufficiently above isobutanol to make the separation by rectification possible with only a few theoretical plates. Extractive distillation typically requires the addition of an equal amount to twice as much extractive agent as the ethanol-isopropanol on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with the isopropanol otherwise it will form a two phase azeotrope with it and some other method of separation will have to be employed.

TABLE 1

Effect of Relative Volatility on the Separation of t-Amyl Alcohol From Isobutanol at 99% Purity.

| Relative Volatility | Theoretical Plates | Actual Plates, 75% Efficiency | Actual Plates, 75% Eff., Min. Reflux |
|---|---|---|---|
| 1.165 | 60 | 80 | 104 |
| 1.4 | 27 | 36 | 47 |
| 1.6 | 20 | 27 | 35 |
| 1.8 | 16 | 22 | 28 |
| 2.0 | 13 | 18 | 24 |
| 2.2 | 12 | 16 | 21 |

The advantage of employing an effective extractive distillation agent for this separation is shown in Table 1. When ordinary rectification is used, 104 actual plates of 75% efficiency are required at minimum reflux ratio to separate t-amyl alcohol from isobutanol in 99% purity. If extractive distillation is employed with an agent that converts the relative volatility to 2.2, only 21 actual plates are required.

A number of investigators have reported the separation of lower boiling alcohols, one from another, by extractive distillation. Carlson, U.S. Pat. No. 2,570,205 used sulfolane to separate n-propanol from butyl alcohols. Carlson, U.S. Pat. No. 2,551,584 used water in a steam distillation on a mixture of lower alcohols but was unable to separate the t-amyl alcohol from isobutanol. They remained in the same fraction. Drout, U.S. Pat. No. 2,552,412 used ethylene glycol, 1,3-propanediol and diethylene glycol as the agents in separating a mixture containing ethanol, sec. butanol, sec. amyl alcohol and t-amyl alcohols. Smith, U.S. Pat. No. 2,559,519 used glycol ethers to separate alcohol mixtures containing ethanol, propanol, isopropanol, and sec. butanol. Smith, U.S. Pat. No. 2,559,520 used ethylene glycol and 1,3-butylene glycol as the extractive agent to separate n-propanol from sec. butanol. Carlson, U.S. Pat. No. 2,575,243 used glycol ether-esters as the agent to separate n-propanol from sec. butanol. Morrell, U.S. Pat. No. 2,591,712 used paraffinic, naphthenic or aromatic hydrocarbon oils to separate close boiling anhydrous alcohols. Morrell, U.S. Pat. No. 2,591,713 used water and a white oil to separate the lower alcohols. Morrell, U.S. Pat. No. 2,706,707 used aqueous solutions of sodium xylene sulfonate or sodium p-cymene sulfonate in the separation of lower alcohols.

OBJECTIVE OF THE INVENTION

The object of this invention is to provide a process or method of extractive distillation that will enhance the relative volatility of t-amyl alcohol from isobutanol in their separation in a rectification column. It is a further objective of this invention to identify organic compounds which are stable, can be separated from isobutanol by rectification with relatively few plates and can be recycled to the extractive distillation column and re-used with little decomposition.

SUMMARY OF THE INVENTION

The objects of this invention are provided by a process for separating t-amyl alcohol from isobutanol which entails the use of certain organic compounds as the agent in extractive distillation.

DETAILED DESCRIPTION OF THE INVENTION

We have discovered that dimethylsulfoxide (DMSO), either singly or in mixtures, will effectively enhance the relative volatility between t-amyl alcohol and isobutanol and permit the separation of pure t-amyl alcohol from isobutanol by rectification when employed as the agent in extractive distillation. Table 2 lists DMSO, its mixtures and the approximate proportions that we have found to be effective. The data in Table 2 was obtained in a vapor-liquid equilibrium still. In each case, the starting material was a 50—50% t-amyl alcohol-isobutanol mixture. The ratios are the parts of extractive agent used per part of t-amyl alcohol-isobutanol mixture. The relative volatilities are listed for each of the two ratios employed. The compound that is effective when used alone is DMSO. The compounds which are effective when used in mixtures of two or more components with DMSO are acetamide, benzoic acid, cinnamic acid, N,N-dimethylacetamide, ethylene glycol, 1,4-butanediol, benzyl propionate, dipropylene glycol dibenzoate, phthalic anhydride, salicylic acid, trimellitic anhydride, tri-2-ethyl hexyl trimellitate, dimethylformamide, hexahydrophthalic anhydride and ethyl benzoate. The ratios in Table 2 are the parts of extractive agent used per part of t-amyl alcohol-isobutanol mixture. The two relative volatilities correspond to the two different ratios. For example in Table 2, one part of DMSO with one part of the t-amyl alcohol-isobutanol mixture gives a relative volatility of 1.8, 6/5 parts of DMSO gives 2.1. One half part of DMSO mixed with one half part of N,N-dimethylacetamide with one part of t-amyl alcohol-isobutanol mixture gives a relative volatility of 1.5, 3/5 parts of DMSO plus 3/5 parts of N,N-dimethylacetamide gives 1.6. One third parts of DMSO plus ⅓ parts of phthalic anhydride plus ⅓ parts of N,N-dimethyl-acetamide mixed with one part of t-amyl alcohol-isobutanol mixture gives a relative volatility of 1.8, with 2/5 parts, these three give 2.0. In every example in Table 2, the starting material is a 50—50% mixture of t-amyl alcohol-isobutanol which possesses a relative volatility of 1.165.

TABLE 2

Extractive Distillation Agents Which Contain Dimethylsulfoxide

| Compounds | Ratios | | Relative Volatilities | |
| --- | --- | --- | --- | --- |
| None | — | | 1.165 | |
| Dimethylsulfoxide (DMSO) | 1 | 6/5 | 1.8 | 2.1 |
| DMSO, Acetamide | (½)² | (3/5)² | 1.5 | 1.5 |
| DMSO, Benzoic acid | " | " | 1.4 | 1.3 |
| DMSO, Cinnamic acid | " | " | 1.4 | 1.4 |
| DMSO, N,N—Dimethylacetamide | " | " | 1.5 | 1.6 |
| DMSO, Ethylene glycol | " | " | 1.5 | 1.4 |
| DMSO, 1,4-Butanediol | " | " | 1.6 | 1.4 |
| DMSO, Benzyl propionate | " | " | 1.4 | 1.4 |
| DMSO, Dipropylene glycol dibenzoate | " | " | 1.4 | 1.4 |
| DMSO, Phthalic anhydride | " | " | 1.5 | 1.4 |
| DMSO, Salicylic acid | " | " | 1.4 | 1.4 |
| DMSO, Trimellitic anhydride | " | " | 1.5 | 1.5 |
| DMSO, Tri-2-ethyl hexyl trimellitate | " | " | 1.4 | 1.4 |
| DMSO, Dimethylformamide (DMFA), Acetamide | (⅓)³ | (2/5)³ | 1.6 | 1.5 |
| DMSO, DMFA, Benzoic acid | " | " | 1.4 | 1.4 |
| DMSO, DMFA, N,N—Dimethylacetamide | " | " | 1.5 | 1.5 |
| DMSO, DMFA, Dipropylene glycol dibenzoate | " | " | 1.4 | 1.4 |
| DMSO, DMFA, Phthalic anhydride | " | " | 1.8 | 2.1 |
| DMSO, DMFA, Hexahydro phthalic anhydride | " | " | 1.4 | 1.5 |
| DMSO, DMFA, Trimellitic anhydride | " | " | 1.6 | 1.7 |
| DMSO, DMFA, Tri-2-ethyl hexyl trimellitate | " | " | 1.5 | 1.4 |
| DMSO, N,N—Dimethylacetamide (DMAC), Acetamide | " | " | 1.7 | 1.5 |
| DMSO, DMAC, Ethyl benzoate | " | " | 1.5 | 1.5 |
| DMSO, DMAC, Phthalic anhydride | " | " | 1.8 | 2.0 |
| DMSO, DMAC, Dipropylene glycol dibenzoate | " | " | 1.4 | 1.4 |
| DMSO, DMAC, Salicylic acid | " | " | 1.4 | 1.4 |
| DMSO, DMAC, Trimellitic anhydride | " | " | 1.6 | 1.5 |
| DMSO, DMAC, Cinnamic acid | " | " | 1.4 | 1.4 |
| DMSO, Acetamide, Trimellitic anhydride | " | " | 1.4 | 1.4 |

TABLE 3

Data From Run Made In Rectification Column.

| Agent | Time Hrs. | Stillpot Temp. °C. At Start | Stillpot Temp. °C. Sampling | Overhead Temp. When Sampling | Wt. % t-Amyl Alc. Overhead | Wt. % t-Amyl Alc. Bottoms | Relative Volatility |
| --- | --- | --- | --- | --- | --- | --- | --- |
| None | 6 | | 106 | 97.5 | 55.8 | 38.5 | 1.165 |
| Dimethysulfoxide | 0.5 | 106 | 118 | 97.5 | 63.3 | 41.9 | 1.21 |
| Dimethysulfoxide | 1.5 | 106 | 121 | 97.5 | 81 | 46.3 | 1.43 |
| Dimethysulfoxide | 2.5 | 106 | 139 | 97.5 | 78.6 | 21.4 | 1.78 |
| Dimethy- | 3.5 | 106 | 167 | 97.5 | 88.9 | 33.3 | 1.85 |

TABLE 3-continued

| Agent | Time Hrs. | Stillpot Temp. °C. At Start | Stillpot Temp. °C. Sampling | Overhead Temp. When Sampling | Wt. % t-Amyl Alc. Overhead | Wt. % t-Amyl Alc. Bottoms | Relative Volatility |
| --- | --- | --- | --- | --- | --- | --- | --- |
| sulfoxide | | | | | | | |

Notes:
Agent feed rate: 20 ml/min; Agent temp.: 85° C.; Boilup rate: 10-20 ml/min.

DMSO listed in Table 2 and whose relative volatility had been determined in the vapor-liquid equilibrium still, was then evaluated in a glass perforated plate rectification column possessing 4.5 theoretical plates. The results are listed in Table 3. The t-amyl alcohol-isobutanol mixture used contained about 45% t-amyl alcohol. The first run is with no extractive agent and with 220 grams of mixture in the stillpot. After six hours of operation, the separation is that in accordance with a relative volatility of 1.165. The second run is with DMSO as the extractive agent. After one-half hour of continuous operation, the relative volatility was 1.21; after 1.5 hours, 1.43; after 2.5 hours, 1.78 and after 3.5 hours, 1.85. Experience with this column has shown that three or more hours of steady operation are required to reach equilibrium. The relative volatility attained, 1.85, can be compared with the 1.8 obtained for DMSO with the vapor-liquid equilibrium still listed in Table 2.

THE USEFULNESS OF THE INVENTION

The usefulness or utility of this invention can be demonstrated by referring to the data presented in Tables 1, 2 and 3. All of the successful extractive distillation agents show that t-amyl alcohol can be removed from isobutanol by means of distillation in a rectification column and that the ease of separation as measured by relative volatility is considerable. Without these extractive distillation agents, virtually no improvement will occur in the rectification column. The data also show that the most attractive agents will operate at a boilup rate low enough to make this a useful and efficient method of recovering high purity t-amyl alcohol from any mixture with isobutanol. The stability of the compounds used and the boiling point difference is such that complete recovery and recycle is obtainable by a simple distillation and the amount required for make-up is small.

WORKING EXAMPLES

EXAMPLE 1

Twenty-five grams of t-amyl alcohol, 25 grams of isobutanol and fifty grams of DMSO were charged to an Othmer type glass vapor-liquid equilibrium still and refluxed for 12 hours. Analysis of the vapor and liquid by gas chromatography gave a vapor composition of 53.1% t-amyl alcohol, 46.9% isobutanol; a liquid composition of 38.6% t-amyl alcohol; 61.4% isobutanol. This indicates a relative volatility of 1.80. Ten grams of DMSO were added and refluxing continued for another eleven hours. Analysis indicated a vapor composition of 47.5% t-amyl alcohol, 52.5% isobutanol; a liquid composition of 30.1% t-amyl alcohol, 69.9% isobutanol which is a relative volatility of 2.10.

EXAMPLE 2

Thirty-three grams of t-amyl alcohol, 67 grams of isobutanol, 25 grams of DMSO and 25 grams of N,N-dimethylacetamide were charged to the vapor-liquid equilibrium still and refluxed for five hours. Analysis indicated a vapor composition of 39.2% t-amyl alcohol, 60.8% isobutanol, a liquid composition of 29.8% t-amyl alcohol, 70.2% isobutanol which is a relative volatility of 1.53. Five grams of DMSO and five grams of N,N-dimethylacetamide were added and refluxing continued for another six hours. Analysis indicated a vapor composition of 38.5% t-amyl alcohol, 61.5% isobutanol; a liquid composition of 29% t-amyl alcohol, 71% isobutanol which is a relative volatility of 1.53.

EXAMPLE 3

Thirty-three grams of t-amyl alcohol, 67 grams of isobutanol, 17 grams of DMSO, 17 grams of N,N-dimethylacetamide and 17 grams of phthalic anhydride were charged to the vapor-liquid equilibrium still and refluxed for 14 hours. Analysis indicated a vapor composition of 33.3% t-amyl alcohol, 66.7% isobutanol; a liquid composition of 21.6% t-amyl alcohol, 78.4% isobutanol which is a relative volatility of 1.82. Three grams each of DMSO, N,N-dimethylacetamide and phthalic anhydride were added and refluxing continued for another ten hours. Analysis indicated a vapor composition of 36.8% of t-amyl alcohol, 63.2% isobutanol and a liquid composition of 22.7% t-amyl alcohol, 77.3% isobutanol which is a relative volatility of 1.98.

EXAMPLE 4

A glass perforated plate rectification column was calibrated with ethylbenzene and p-xylene which possesses a relative volatility of 1.06 and found to have 4.5 theoretical plates. A solution of 100 grams of t-amyl alcohol and 100 grams of isobutanol was placed in the stillpot and heated. The column was operated at total reflux for six hours to establish equilibrium throughout. Overhead and bottoms samples of approximately 2 ml. were collected and analysed by gas chromatography. The overhead analysis was 55.8% t-amyl alcohol, 44.2% isobutanol and the stillpot analysis was 38.5% t-amyl alcohol and 61.5% isobutanol. Using these compositions in the Fenske equation with the number of theoretical plates in the column being 4.5, gave an average relative volatility of 1.165 for each theoretical plate. An extractive agent consisting of DMSO was then pumped into the column at a rate of 20 ml/min. The temperature of the extractive agent as it entered the column was 85° C. After establishing the feed rate of the extractive agent, the heat input to the t-amyl alcohol-isobutanol in the stillpot was adjusted to give a reflux rate of 10-20 ml/min. After one half hour of operation, overhead and bottoms samples were collected and analysed. The overhead analysis was 63.3% t-amyl alcohol, 36.7% isobutanol and the bottoms analysis was 41.9% t-amyl alcohol, 58.1% isobutanol which gave an average relative volatility of 1.21 for each theoretical plate. After 1.5 hours of total operating time, the overhead and bottoms samples were again taken and analysed. The overhead composition was 81% t-amyl alcohol, 19% isobutanol and the bottoms composition was 46.3% t-amyl alcohol, 53.7% isobutanol. This gave an average relative volatility of 1.43 for each theoretical plate. After 2.5 hours of total operating time, the overhead and bottoms samples were again taken and analysed. The overhead composition was 78.6% t-amyl alcohol, 21.4% isobutanol and the bottoms composition was 21.4% t-amyl alcohol, 78.6% isobutanol. This gave an average relative volatility of 1.78 for each theoretical plate. After 3.5 hours of total operating time, the overhead analysed 88.9% t-amyl alcohol, 11.1% isobutanol and the bottoms analysed 33.3% t-amyl alcohol, 66.7% isobutanol which is a relative volatility of 1.85 for each theoretical plate. The data in this example are summarized in Table 3.

We claim:

1. A method for recovering t-amyl alcohol from a mixture of t-amyl alcohol and isobutanol which comprises distilling a mixture of t-amyl alcohol and isobutanol in a rectification column in the presence of about one to two parts of extractive agent per part of t-amyl alcohol-isobutanol mixture, recovering the t-amyl alcohol as overhead product and obtaining the extractive agent and isobutanol from the stillpot, the extractive agent comprises dimethylsulfoxide.

2. The method of claim 1 in which the extractive agent comprises dimethylsulfoxide and at least one material from the group consisting of acetamide, benzoic acid, cinnamic acid, N,N-dimethylacetamide, ethylene glycol, 1,4-butanediol, benzyl propionate, dipropylene glycol dibenzoate, phthalic anhydride, salicylic acid, trimellitic anhydride, tri-2-ethyl hexyl trimellitate, dimethylformamide, hexahydrophthalic anhydride and ethylbenzoate.

* * * * *